(12) United States Patent
Frost et al.

(10) Patent No.: US 7,786,096 B2
(45) Date of Patent: *Aug. 31, 2010

(54) INHIBITION OF ANTIGEN PRESENTATION WITH POORLY CATABOLIZED POLYMERS

(75) Inventors: Greogry I. Frost, Solana Beach, CA (US); Per Borgstrom, La Jolla, CA (US)

(73) Assignee: Halozyme, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/463,315

(22) Filed: May 8, 2009

(65) Prior Publication Data

US 2009/0215722 A1 Aug. 27, 2009

Related U.S. Application Data

(62) Division of application No. 10/381,855, filed as application No. PCT/US01/42329 on Sep. 25, 2001, now Pat. No. 7,538,097.

(60) Provisional application No. 60/235,321, filed on Sep. 26, 2000.

(51) Int. Cl.
 *A61K 31/721* (2006.01)
 *A61K 38/00* (2006.01)
(52) U.S. Cl. .......................... 514/59; 514/11; 424/572; 424/93.21
(58) Field of Classification Search .................. None
 See application file for complete search history.

(56) References Cited

U.S. PATENT DOCUMENTS

| 5,852,003 A | 12/1998 | Barritault et al. | |
|---|---|---|---|
| 7,538,097 B2 * | 5/2009 | Frost et al. ..................... | 514/59 |

FOREIGN PATENT DOCUMENTS

| EP | 0 375 976 A2 | 7/1990 |
|---|---|---|
| FR | 2 651 436 A1 | 3/1991 |
| FR | 2 657 782 A1 | 8/1991 |
| WO | WO 99/29328 A1 | 6/1999 |
| WO | WO 00/76452 A2 | 12/2000 |

OTHER PUBLICATIONS

Schlegel et al, Proc Natl Acad Sci USA 93: 5061-5066, May 1996.*
Thomas et al, Transplantation Proceedings 28(2): 593-594, Apr. 1996.*
Leyva-Cobian et al, J Immunology 141: 1445-1450, 1988.*
Moreno et al, Immunology 33: 261-267, 1977.*
Arnold et al., "Modulation of T Lymphocyte Controlled Functions by Dextran Sulfate", *Clinical Research*, 26(5):729A (1978).
Babcock et al., "Suppression of cell-mediated immune responses by dextran sulphate", *Immunology*, 33(6):925-929 (1977).
Berthiaume et al., "Molecular size-fractionation during endocytosis in macrophages", *J. Cell Biol.*, 129(4): 989-998 (1995).
Careaga-Reyna et al., "Effect on Acute Rejection Reaction and Survival of the Heart with the Additional of Dextran 60 to Conventional Immunosuppressive Therapy in an Experimental Model of Heterotopic Heart Transplantation", *Arch. Med. Res.*, 31(1):37-41 (2000).
Janeway et al., "Immunobiology: The Immune System in Health and Disease", Current Biology Ltd./Garland Publishing Inc., UK, p. 1140-1141 (1994).
Khanna et al, "Donor bone marrow potentiates the effect of tacrolimus on nonvascularized heart allograft survival: association with microchimerism and growth of donor dendritic cell progenitors from recipient bone marrow", *Transplantation*, 65(4): 479-485 (1998).
Moreno et al, "The mitogenic, immunogenic and tolerogenic properties of dextrans and levans. Lack of correlation according to differences of molecular structure and size", *Immunology*, 33(2):261-267 (1977).
Oh et al, "Different fates of phagocytosed particles after delivery into macrophage lysosomes", *J. Cell Biology*, 132(4): 585-593 (1996).
Schlegel et al, "A synthetic random basic copolymer with promiscuous binding to class II major histocompatibility complex molecules inhibits T-cell proliferative responses to major and minor histocompatibility antigens in vitro and confers the capacity to prevent murine graft-versus-host disease in vivo", *Proc. Natl. Acad. Sci. USA*, 93(10): 5061-5066 (1996).
Thomas et al., "A Synthetic Dextran Derivative Inhibits Complement Activation and Complement-Mediated Cytotoxicity in an In Vitro Model of Hyperacute Xenograft Rejection", *Transplant Proc.*, 28(2):593-594 (1996).
Thomas et al., "Effect of substituted dextran derivative on complement activation in vivo", *Biomaterials*, 16(15):1163-1167 (1995).
Thomas et al., "Sulfonated Dextran Inhibits Complement Activation and Complement-Dependent Cytotoxicty in an In Vitro Model of Hyperacute Xenograft Rejection", *Mol. Immunol.*, 33(7-8):643-648 (1996).

* cited by examiner

*Primary Examiner*—Phuong Huynh
(74) *Attorney, Agent, or Firm*—DLA Piper LLP (US)

(57) ABSTRACT

Methods to prevent the rejection of immunogenic tissues in an animal by administering a non-immunogenic, poorly catabolized molecule in an amount sufficient to inhibit an immune response are described herein. Also described are compositions that are useful for inhibiting immune responses in animals that are recipients of cellular transplants. For example, these methods and compositions can be used to prevent the rejection of xenografted and allografted tissues in an animal.

12 Claims, 6 Drawing Sheets

INHIBITION OF ANTIGEN PRESENTATION WITH POORLY CATABOLIZED POLYMERS

CROSS REFERENCE TO RELATED APPLICATIONS

This application is a divisional application of U.S. application Ser. No. 10/381,855 filed Oct. 8, 2003, now U.S. Pat. No. 7,538,097; which is a 35 USC §371 National Stage application of International Application No. PCT/US01/42329 filed Sep. 25, 2001; which claims the benefit under 35 USC §119(e) to U.S. Application Ser. No. 60/235,321 filed Sep. 26, 2000, now abandoned. The disclosure of each of the prior applications is considered part of and is incorporated by reference in the disclosure of this application.

BACKGROUND OF INVENTION

1. Field of the Invention

The present invention relates to the field of immunosuppression, more specifically to methods of inhibiting antigen presentation and transplant rejection.

2. Background Information

A number of diseases are treated by the transplantation of tissue donated by other humans (allografts) or obtained from animals (xenografts). For example, insulin-dependent diabetes is often treated by transplantation of insulin-secreting pancreatic islet cells. While the transplanted cells may have the capacity to perform the desired function (e.g., secretion of insulin in response to rising levels of glucose), such grafts typically fail as a result of immunological rejection. Shortly after transplantation, cells of the immune system of the recipient recognize the allogeneic or xenogeneic cells as foreign and proceed to attack the graft through both humoral and cellular routes. Allogeneic or xenogeneic cells are initially recognized by the recipient's immune system through antigenic determinants expressed on the surface of the cells. The predominant antigens recognized as "non-self" are major histocompatibility complex class I and class II antigens (MHC class I and class II). MHC class I antigens are expressed on virtually all parenchymal cells (e.g., pancreatic islet cells), in contrast, MHC class II antigens are expressed on a limited number of cell types, primarily B cells, macrophages, dendritic cells, Langerhans cells and thymic epithelium. The interaction of foreign MHC antigens with the T cell receptor on host T cells causes these cells to become activated. Following activation, the T cells proliferate and induce effector functions which result in cell lysis and destruction of the transplanted cells.

For transplantation to be a viable therapeutic option, approaches are needed to inhibit rejection of transplanted cells by the immune system of the recipient. One method for inhibiting this rejection process is by administration of drugs that suppress the function of the immune system. While drugs such as cyclophosphamide and cyclosporin effectively inhibit the actions of the immune system and thus allow graft acceptance, their use can cause generalized, non-specific immunosuppression in the graft recipient which leaves the recipient susceptible to other disorders such as infection and tumor growth. Additionally, administration of immunsuppressive drugs is often accompanied by other serious side effects such as renal failure and hypertension.

It has been shown that it is possible to alter an antigen on the surface of a cell prior to transplantation to "mask" the antigen from normal recognition by cells of the recipient's immune system (see, Faustman and Coe, *Science* 252:1700-1702 (1991) and WO 92/04033). For example, MHC class I antigens on transplanted cells can be altered by contacting the cells with a molecule which binds to the antigen, such as an antibody or fragment thereof (e.g., a F(ab')2 fragment) prior to transplantation. This alteration of MHC class I antigens modifies the interaction between the antigens on the cells and T lymphocytes in the recipient following transplantation to thereby inhibit rejection of the transplanted cells. Additional methods for reducing the immunogenicity of an allograft or xenograft to inhibit rejection of the graft following transplantation in a host are needed.

T-cell mediated immune responses are thought to be the primary mechanism of organ transplant rejection and a driving component of various auto-immune diseases. This T-cell mediated immune response is initially triggered by helper T-cells which are capable of recognizing specific antigens. These helper T-cells may be memory cells left over from a previous immune response or naive cells which are released by the thymus and may have any of an extremely wide variety of antigen receptors. When one of these helper T-cells recognizes an antigen present on the surface of an antigen presenting cell (APC) or a macrophage in the form of an antigen-MHC complex, the helper T-cell is stimulated by signals emanating from the antigen-specific T-cell receptor, co-receptors, and IL-1 secreted by the APC or macrophage, to produce IL-2. The helper T-cells then proliferate. Proliferation results in a large population of T-cells which are clonally selected to recognize a particular antigen. T-cell activation may also stimulate B-cell activation and nonspecific macrophage responses. Some of these proliferating cells differentiate into cytotoxic T-cells which destroy cells having the selected antigen. After the antigen is no longer present, the mature clonally selected cells will remain as memory helper and memory cytotoxic T-cells, which will circulate in the body and recognize the antigen should it show up again. If the antigen triggering this response is not a foreign antigen, but a self antigen, the result is auto immune disease; if the antigen is an antigen from a transplanted organ, the result is graft rejection. Consequently, it is desirable to be able to regulate this T cell mediated immune response.

The current paradigms of immunosuppressive agents reflects the progress in understanding the cellular and molecular mechanisms which mediate graft rejection. Six paradigms represent the evolution of immunosuppressive strategies for organ transplantation to date. The proliferation paradigm advances agents which interrupt lymphocyte cell division (azathioprine, cyclophosphamide, mycophenolic acid). The depletion paradigm conscripts drugs that bind to lymphocyte cell surface markers, thereby producing cell lysis and/or inactivation (polyclonal ATGAM and thymoglobulin, and monoclonal OKT3 antilymphocyte antibodies). The cytokine paradigm uses agents that interrupt lymphocyte maturational events; eg, synthesis (calcineurin inhibitors; cyclosporine/tacrolimus), binding to surface receptors (anti-CD25 mAbs), or signal transduction phases of cytokine stimulation (sirolimus). The introduction of calcineurin inhibitors markedly reduces the rate of acute rejection episodes and increases short-term graft survival rates; nephrotoxicity and chronic allograft attrition remain as unanswered challenges. The cyclosporine A (CsA) sparing property of sirolimus permits the use of lower exposure to calcineurin agents, allows for early withdrawal of steroid therapy, and may delay allograft senescence. Furthermore, the combination of SRL with anti-IL-2R mAbs proffers an induction approach which allows prolonged periods of holiday from calcineurin inhibitors. To address the tissue nonselectivity of the calcineurin and mTOR inhibitors, which presumably causes the drug toxicities, new agents are being developed to selectively inhibit the T cell target Janus Kinase 3. In the co-stimulation paradigm, the accessory signals generated by antigen-presenting cells are interrupted by distinct agents: the receptor conjugate CTLA4-immunoglobulin and anti-B7 or anti-CD40 ligand mAbs. Another set of drugs (selectin blocking agents, anti-ICAM-1 antisense deoxy oligonucleotides, and the lymphocyte homing inhibitor FTY720) seeks to modulate the ischemia-reperfusion injury, which exacerbates cytokine-mediated events in the donor and the subsequent procurement injury and may also accelerate the progression of transplant senescence. Finally, the transplantation tolerance paradigm is based on the development of strategies which distort alloimmune recognition by antigen reactive cells (MHC peptides or proteins), produce anergy (costimulation blockers), functional inactivation, or deletion of antigen-reactive cells (donor bone marrow infusions and gene therapy).

Thus, the common paradigms today focus upon either T-cell expansion or extravasation into the rejected tissue site. However, a relatively ignored component of immune rejection is antigen presentation, which we now document herein as an excellent target for intervention through the use of poorly catabolized polymers.

SUMMARY OF THE INVENTION

The present invention relates to the discovery that foreign antigen presentation can be inhibited in an animal by saturating the antigen presenting cells (APC's) with non immunogenic agents. In general, methods are provided to saturate antigen-presenting cells with poorly catabolized non immunogenic-polymers that are readily phagocytosed by APC's such that the presentation of immunogenic foreign antigens are effectively inhibited.

One embodiment of the present invention provides a method of inhibiting antigen presentation in an animal by administering to an animal a poorly catabolized polymer in an amount sufficient to inhibit presentation of at least one antigen to the immune system of the animal. The at least one antigen can be derived from a variety of sources such as, but not limited to, allografted cells, xenografted cells, isolated stem cells and gene therapy formulations. Furthermore, the at least one antigen can be derived from a source that is substantially free of nucleic acid.

Another embodiment of this invention provides a method of inhibiting the rejection of cells transplanted in animals by administering a poorly catabolized polymer to an animal then introducing, into the animal, cells that are capable of expressing at least one antigen. Cells that are capable of expressing at least one antigen can be but are not limited to allografted cell, xenografted cells and isolated stem cells.

Yet another embodiment of the present invention provides a method of inhibiting an immune response to a gene therapy formulation by administering a poorly catabolized polymer to an animal then introducing, into the animal, a gene therapy formulation that is capable of producing at least one antigen.

In each of the previously described methods, the time of administration of the poorly catabolized polymer can be altered. Specifically, the poorly catabolized polymer can be administered to the animal before at least one antigen is presented the immune system of the animal. The poorly catabolized polymer can also be administered to the animal before exposing the animal to at least one antigen. Even more specifically, the poorly catabolized polymer is administered to the animal more than 24 hours prior to exposing the animal to at least one antigen.

Other embodiments of this invention describe administration of the poorly catabolized polymer to an animal in the presence of other immunosuppressive agents. In still other embodiments the poorly catabolized polymer comprises a dextran solution.

The present invention also provides a pharmaceutical composition comprising a poorly catabolized polymer wherein the poorly catabolized polymer is used to inhibit the presentation of at least one antigen to the immune system of an animal. In some of these compositions, the poorly catabolized polymer comprises a dextran solution.

Still another embodiment of the present invention provides a use of a poorly catabolized polymer in the preparation of a medicament for treating rejection by the immune system of an antigenic material introduced into an animal. This antigenic material can comprise a cell. It can also comprise a gene therapy formulation. In some uses, the poorly catabolized polymer is dextran.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein.

DETAILED DESCRIPTION OF THE PREFERRED EMBODIMENT

Figure 1:
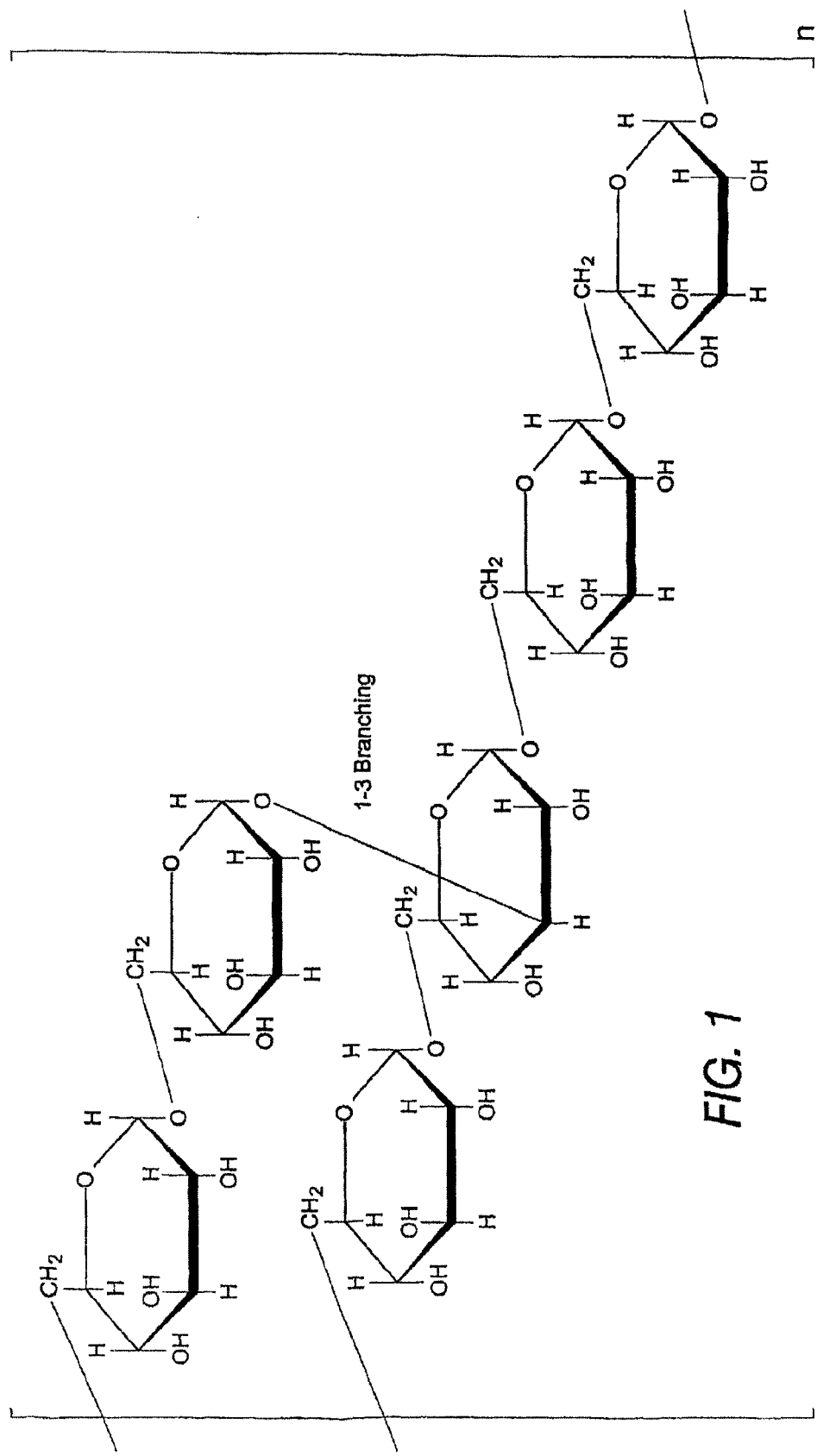
FIG. 1 is a schematic which illustrates the chemical structure of a portion of a dextran polymer.

Dextran is a polymer of anhydroglucose. FIG. 1 shows the unit structure of a typical a polymer of dextran. Approximately 95% of the dextran polymer is composed of D-glucose molecules having $\alpha(1 \rightarrow 6)$ linkages (Rankinet et al., *J. Am. Chem. Soc.* 76:4435 (1954)). The remaining 5% is composed of glucose molecules linked together by $\alpha(1 \rightarrow 3)$ glycosidic bonds. These $\alpha(1 \rightarrow 3)$ linkages account for the branching of the dextran polymer. Conflicting data on the branch lengths implies that the average branch length is less than three glucose units. However, other methods indicate branches of greater than 50 glucose units exist.

The molecular weight of a dextran polymer affects its structure. Native dextran has been found to have a molecular weight (MW) in the range of 9 million to 500 million Daltons (Da). This molecular weight range corresponds roughly to dextrans having between 50,000 and 2.8 million glucose molecules. Many of the more commonly used dextrans are of lower MW than the native polymers. These lower MW dextrans exhibit slightly less branching and have a more narrow range of MW distribution than the native polymers. Dextrans with MW greater than 10,000 glucose molecules behave as if they are highly branched. However, as the MW increases, dextran molecules attain greater symmetry. Dextrans with MW of 2,000 to 10,000 glucose molecules exhibit the properties of an expandable coil. At MWs below 2,000 glucose molecules, dextran is more rod-like.

There are a variety of techniques that are commonly used to determine the MW of dextran polymers. For example, the MW of dextran can be measured by one or more of the following methods: low angle laser light scattering, size exclusion chromatography, copper-complexation and anthrone reagent colorometric reducing-end sugar determination and viscosity.

Most dextrans are derived from *Leuconostoc mesenteroides*, strain B 512. Shorter dextran polymers of various MWs are then produced by limited hydrolysis and fractionation although exact methods are held proprietary. In general, however, fractionation of these polymers can be accomplished by size exclusion chromatography or ethanol fractionation in which the largest MW dextrans precipitate first.

Pharmaceutically acceptable compositions contemplated for use in the practice of the present invention can be used in the form of a solid, a solution, an emulsion, a dispersion, a micelle, a liposome, and the like, wherein the resulting composition contains one or more of the active compounds contemplated for use herein, as active ingredients thereof, in admixture with an organic or inorganic carrier or excipient suitable for nasal, enteral or parenteral applications. The active ingredients may be compounded, for example, with the usual non-toxic, pharmaceutically or physiologically acceptable carriers for tablets, pellets, capsules, troches, lozenges, aqueous or oily suspensions, dispersible powders or granules, suppositories, solutions, emulsions, suspensions, hard or soft capsules, caplets or syrups or elixirs and any other form suitable for use. In addition auxiliary, stabilizing, thickening and coloring agents may be used. The active compounds contemplated for use herein are included in the pharmaceutical composition in an amount sufficient to produce the desired effect upon the target process, condition or disease.

In addition, such compositions may contain one or more agents selected from flavoring agents (such as peppermint oil of wintergreen or cherry), coloring agents, preserving agents, and the like, in order to provide pharmaceutically elegant and palatable preparations. Tablets containing the active ingredients in admixture with non-toxic pharmaceutically acceptable excipients may also be manufactured by known methods. The excipients used may be, for example, (1) inert diluents, such as calcium carbonate, lactose, calcium phosphate, sodium phosphate, and the like; (2) granulating and disintegrating agents, such as corn starch, potato starch, alginic acid, and the like; (3) binding agents, such as gum tragacanth, corn starch, gelatin, acacia, and the like; and (4) lubricating agents, such as magnesium stearate, stearic acid, talc, and the tike. The tablets may be uncoated or they may be coated by known techniques to delay disintegration and absorption in the gastrointestinal tract, thereby providing sustained action over a longer period. For example, a time delay material such as glyceryl monostearate or glyceryl distearate may be employed. The tablets may also be coated by the techniques described in the U.S. Pat. Nos. 4,256,108; 4,160,452; and 4,265,874 to form osmotic therapeutic tablets for controlled release.

When formulations for oral use are in the form of hard gelatin capsules, the active ingredients may be mixed with an inert solid diluent, for example, calcium carbonate, calcium phosphate, kaolin, or the like. They may also be in the form of soft gelatin capsules wherein the active ingredients are mixed with water or an oil medium, for example, peanut oil, liquid paraffin, olive oil and the like.

Formulations may also be in the form of a sterile injectable suspension. Such a suspension may be formulated according to known methods using suitable dispersing or wetting agents and suspending agents. The sterile injectable preparation may also be a sterile injectable solution or suspension in a non-toxic parenterally-acceptable diluent or solvent, for example, as a solution in 1,4-butanediol. Sterile, fixed oils are conventionally employed as a solvent or suspending medium. For this purpose, any bland fixed oil may be employed including synthetic mono- or diglycerides, fatty acids (including oleic acid), naturally occurring vegetable oils like sesame oil, coconut oil, peanut oil, cottonseed oil, etc., or synthetic fatty vehicles like ethyl oleate or the like. Buffers, preservatives, antioxidants, and the like can be incorporated as required.

Formulations contemplated for use in the practice of the present invention may also be administered in the form of suppositories for rectal administration of the active ingredients. These compositions may be prepared by mixing the active ingredients with a suitable non-irritating excipient, such as cocoa butter, synthetic glyceride esters of polyethylene glycols (which are solid at ordinary temperatures, but liquify and/or dissolve in the rectal cavity to release the active ingredients), and the like.

In addition, sustained release systems, including semi-permeable polymer matrices in the form of shaped articles (e.g., films or microcapsules) can also be used for the administration of the active compound employed herein. The poorly catabolized polymer can also be provided as a unit dosage such as a septum-sealed vial, either lyophilized or in aqueous solution.

EXAMPLES

The following examples are put forth so as to provide those of ordinary skill in the art with a complete disclosure and description of how to carry out the invention. The examples are not intended to limit the scope of what the inventors regard as their invention. Efforts have been made to ensure accuracy with respect to the numbers disclosed herein (e.g. amounts, temperatures, etc.); however, those skilled in the art will account for some experimental error and deviation. Unless indicated otherwise, molecular weights are reported as average molecular weight.

Example 1

Inhibition of Xenograft Tissue Rejection Through Pre-Treatment with a Dextran Polymer Dextran, derived from *Leuconostoc mesenteroides*, strain B512 (average Molecular Weight 500,000 Da) was used in the following studies. A dextran solution, suitable for administration to animals, was made by dissolving solid dextran in sterile deionized water ($dH_2O$) to a final concentration of 10%.

For cellular implants into mice, human HT1080 spheroids expressing green fluorescent protein were used. These spheroids were prepared using the following method. Histone H2B-GFP, prepared as previously described (Kanda, et al., *Curr. Biol.* 26:377-85 (1998)), was subcloned into the LXRN retroviral vector (Clontech, Palo Alto Calif.). The resultant H2B-GFP LXRN vector was cotransfected with VSVG into GP-293 cells (Clontech) and viral supernatants harvested 48 hours post transaction. Retroviral supernatants were concentrated by centrifugation at 50,000 g and stored at −80° C. until use. HT1080 cells (obtained from ATCC) or IPSC (pancreatic beta stem cells (provided by Ixlon Biotechnology, Alachua, Fla.)) were transduced with VSVG pseudotyped H2BGFP LXRN virus stocks for 48 hours with 5 µg/ml polybrene and were selected in 300 µg/ml G418 for 2 weeks. Pooled cells that expressed H2BGFP, as determined by fluorescent microscopy and FACs analysis, were expanded and used for in vivo experiments. HT1080 cells were passaged in DMEM 4.5 g/L glucose supplemented with pyruvate, glutamine, non-essential amino acids, and gentamicin (50 µg/ml) and maintained in a humidified 5% $CO_2$ atmosphere at 37° C. Cells were routinely tested for mycoplasma contamination with the Genprobe mycoplasma detection kit. Suspensions of trypsinized monolayers were washed with fresh complete medium viability tested with trypan blue exclusion, and diluted to a final volume of 250,000 cells/ml. The cell suspensions were dispersed 100 ul/well into 96 well round bottom plates coated with 1.0% agarose for a liquid overlay. The spheroids were allowed to compact for 48 hours followed by washing in serum free media for implantation into mice bearing titanium chambers.

C57B1/6 mice were prepared by surgically implanting titanium chambers into a dorsal skinfold as described previously, (see, Lehr, et al., *Am. J. Pathol.* 143:1055-1062 (1993); Torres et. al., *Microvascular Research* 49:212-226 (1995)). In brief, male mice (25-35 g body weight) were anesthetized (7.3 mg ketamine hydrochloride and 2.3 mg xylazine /100 g body weight, i.p.) and placed on a heating pad. Two symmetrical titanium frames were implanted into a dorsal skinfold, so as to sandwich the extended double layer of skin. A 15 mm full thickness skin layer was excised. The underlying muscle (M. cutaneous max.) and subcutaneous tissues were covered with a glass cover slip incorporated in one of the frames.

After a recovery period of 2-5 days, the mice were divided into both treatment and control groups. A 200 µl injection of the sterile 10% dextran solution was administered to the treatment group intravenously through the tail vein 48 hours prior to spheroid implantation. Equivalent injections of $dH_2O$ were administered to control group mice. A second 200 µl injection of the sterile 10% dextran solution was administered to the treatment group 24 hours after the first injection, whereas the control group received $dH_2O$. On the day of implantation, an equivalent number of HT1080 spheroid cells expressing green fluorescent protein were implanted into the titanium chambers of both the control and treatment group mice. Subsequent to spheroid implantation, and for the duration of the experiment, 100 µl of the 10% sterile dextran solution was administered to each mouse in the treatment group intravenously through the tail vein at 24 hour intervals. Equivalent injections of $dH_2O$ were administered to the control mice. Throughout the course of the experiment, the size of HT1080 cell xenografts were measured by fluorescent intravital microscopy. This microscopy was performed using a Mikron Instrument Microscope (Mikron Instrument, San Diego, Calif.) equipped with epi-illuminator and video-triggered stroboscope illumination from a xenon arc (MV-7600, EG&G, Salem, Mass.). A silicon intensified target camera (SIT68, Dage-MTI, Michigan City, Ind.) was attached to the microscope. A Hamamatsu image processor (Argus 20) with firmware version 2.50 (Hamamatsu Photonic System, USA) was used for image enhancement and to capture images to a computer. A Leitz PL1/0.04 objective was used to obtain an over-view of the chamber and for determination of graft size.

Statistical analysis was made using a statistical software package (SigmaStat, Jandel Scientific). Statistical analysis was made using both analysis of variance and multiple comparison tests. For all tests, p values smaller than 5% were considered significant. Data was presented as MEAN±STD.

Figure 2:
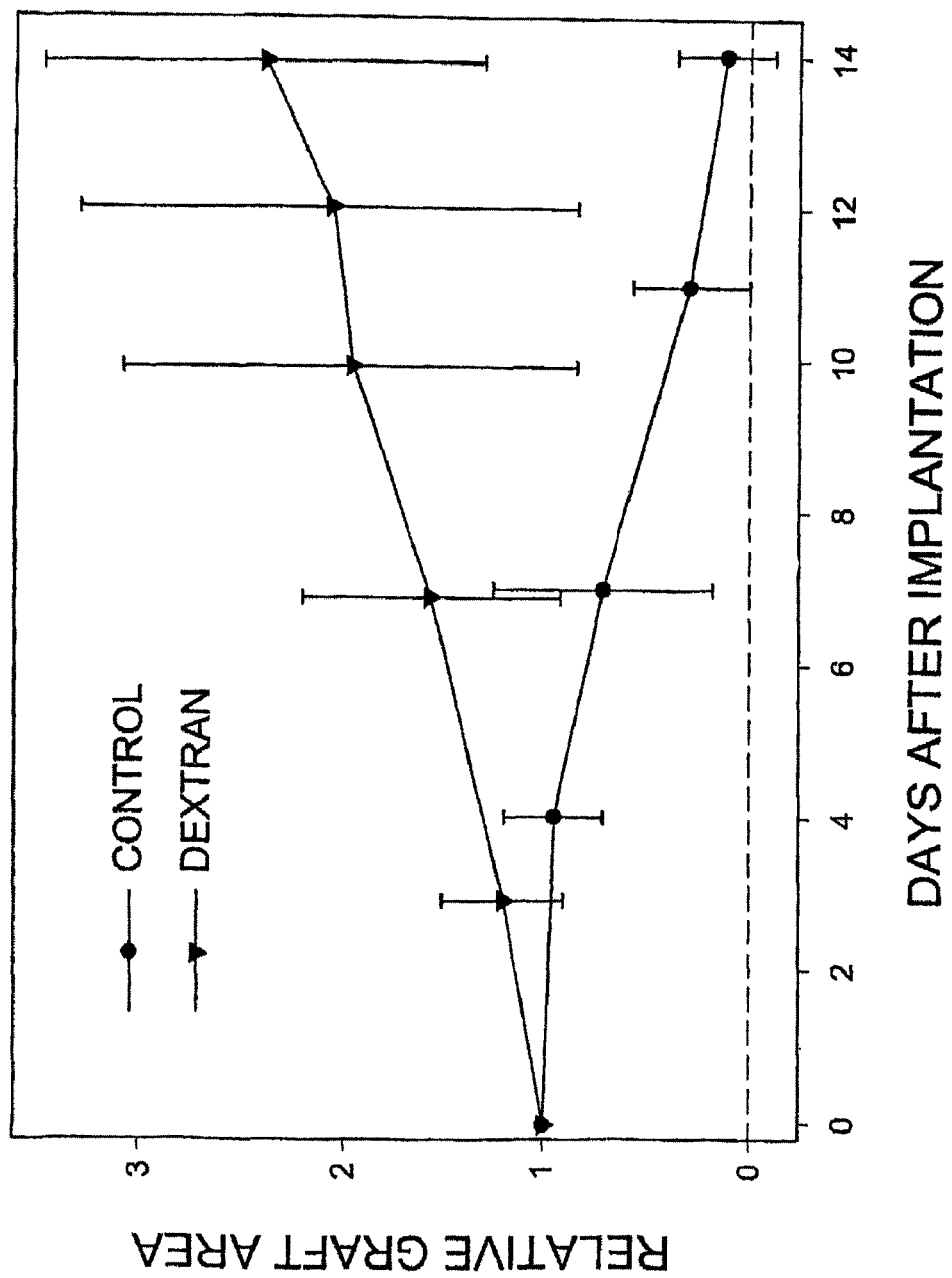
FIG. 2 is a graph which shows the effect of pre-administration of a dextran solution on the survival of human HT1080 cell xenografts that are grown inside titanium chambers which have been implanted in C57BI/6 mice.

FIG. 2 plots the survival of the HT1080 spheroid xenografts for both dextran-treated mice and the control group. For the mice treated with dextran, the size of the HT1080 xenograft increases throughout the course of the experiment. By the end of the experiment, on day 14, the size of the xenograft has more than doubled. By contrast, the xenografts in the control mice decrease throughout the course of the experiment and have been eliminated by day 14. These results indicate that pretreatment with 10% dextran solution for 48 hours prior to transplantation results in effective inhibition of xenograft rejection.

Example 2

Effects of the Route of Administration of the Dextran Polymer on Xenograft Survival To examine the temporal and spatial dependence of the dextran polymer on graft survival, dextran was administered intraperitoneally (i.p.) verses intraveneously (i.v.). The methodology of Example 1 was used with the following modifications. C57B1/6 mice having implanted titanium chambers were divided into four groups. The first group was designated as the control group and received no treatment. The second group received 200 µl i.p. injections of the sterile 10% dextran solution every 24 hours beginning two days prior to spheroid implantation. On the day of spheroid implantation and thereafter, the injection volume was reduced to 100 µl. The third group of mice received 100 µl i.v. injections of the sterile 10% dextran solution every 24 hours beginning four days after spheroid implantation. The fourth group (designated the Re-Implant group) was comprised of mice that had rejected a spheroid xenograft that had been implanted 10 previously. This group received i.v. dextran treatments beginning six day prior to re-implantation of spheroids. On the first and second day of treatment, a 200 µl volume of the sterile dextran solution was administered. On each day thereafter, the volume was decreased to 100 µl. These 100 µl injections were continued throughout the course of the experiment.

Figure 3:
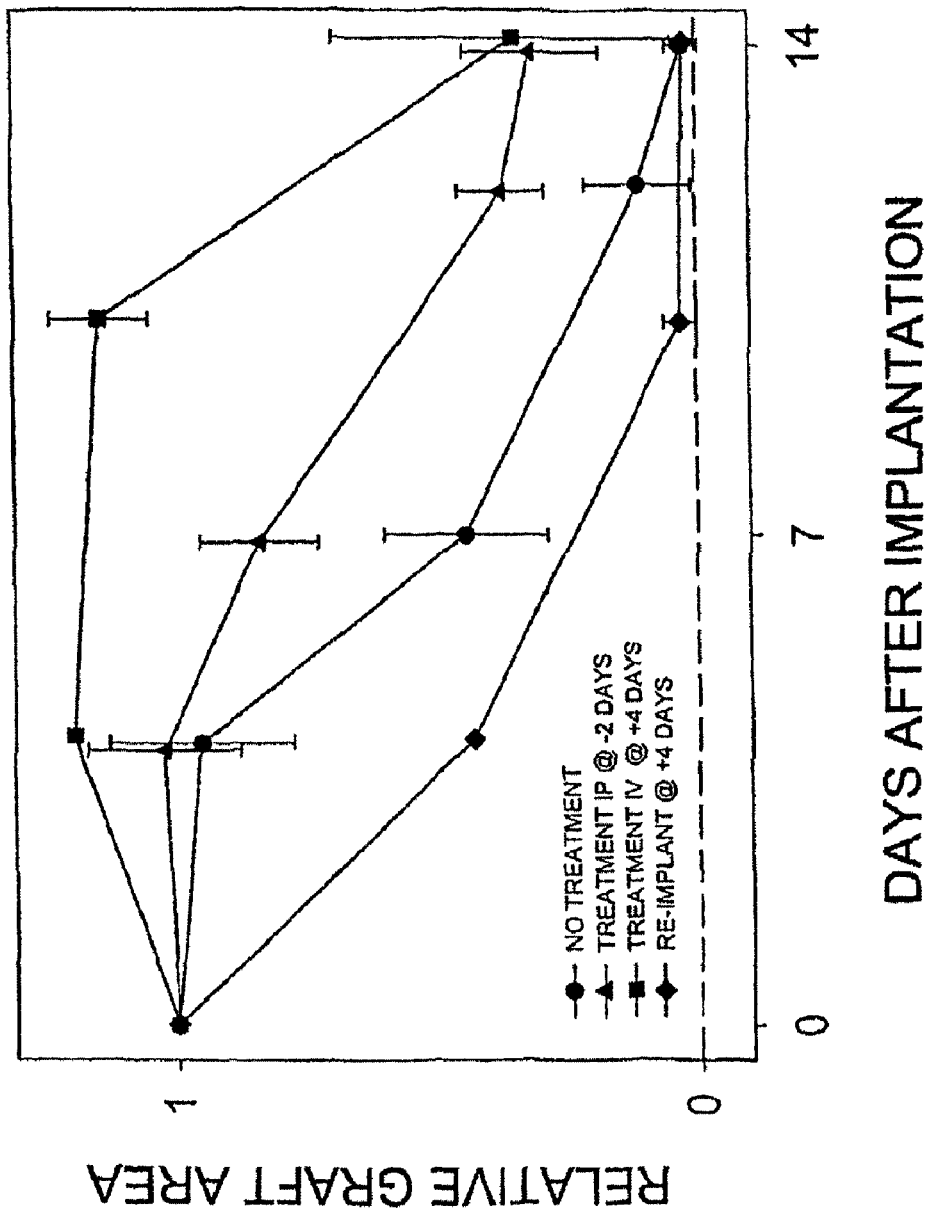
FIG. 3 is a graph which shows the effect of the route of dextran administration on the survival of human HT1080 cell xenografts that are grown inside titanium chambers which have been implanted in C57BI/6 mice.

FIG. 3 shows the xenograft survival over the 14 day course of the experiment for each group of mice. By day 14, every group has experienced a significant reduction in xenograft size. In contrast with the i.v. dextran pretreatments described in Example 1, i.p. administration of dextran beginning 48 hours prior to implantation (group 2) did not enhance the survival of xenografts. Similarly, xenograft survival was not enhanced by i.v. treatments commencing four days after spheroid implantation (group 3). This result suggests that the mechanism by which dextran acts is not through inhibition of the ability of T-cells to extravasate into the chamber.

FIG. 3 also shows that dextran pretreatment could not protect spheroids which had been implanted into mice that had previously rejected a spheroid graft (group 4). By day 10 of the experiment, the spheroid graft was eliminated. Accordingly, this result eliminates the possibility of direct T-cell inhibition as a mechanism of suppression.

Example 3

The Effect of Dextran Uptake on Antigen Presenting Cells

The uptake of dextran by APCs was shown by injecting mice with fluorescein isothiocyanate (FITC) labeled dextran then visualizing tissue sections by fluorescent microscopy. C57/B16 mice were divided into two groups. Mice in the first group received a 200 µl i.v. injection of a 2% FITG labeled dextran solution (average MW of dextran 500,000 Da). Twenty-four hours later, the animals were sacrificed and organ sections were whole mounted and imaged using fluorescent microscopy. Mice in the second group received a 200 µl i.v. injection of an unlabeled 10% dextran solution one daily for 48 hours. At the end of the 48 hour period, the mice were given a 200 µl i.v. injection of the 2% FITC labeled dextran solution. Twenty-four hours later, these animals were subjected to the same treatment as mice in the first group.

Analysis of the tissues of mice in the first group revealed macrophage-like cells taking up the labeled dextran polymer in all tissues examined including brain, lung, spleen, kidney, peritoneum, lymph-nodes, skin, and liver. Analysis of the tissues of mice in the second group revealed no labeling which indicated that saturation of these cells with the unlabeled polymer had occurred. The conclusion from these studies was that perturbation of antigen presenting cell function was the principal mechanism by which this poorly catabolized polymer blocked transplant rejection.

Example 4

Temporal Optimization of Dextran Administration for the Survival of Xenografts in Mice To demonstrate the temporal effect of dextran administration on xenografts, the methodology of Example 1 was used with the following modifications. C57B1/6 mice having implanted titanium chambers were divided into three groups. The first group was designated as the control group and received no treatment. The second group received 200 µl i.v. injections of the sterile 10% dextran solution every 24 hours beginning two days prior to spheroid implantation. On the day of spheroid implantation and thereafter, the injection volume was reduced to 100 µl. The third group received a 200 µl i.v. injection of the sterile 10% dextran solution 24 hours prior to spheroid implantation. On the day of spheroid implantation and every 24 hours thereafter, 100 µl injections were given.

Figure 4:
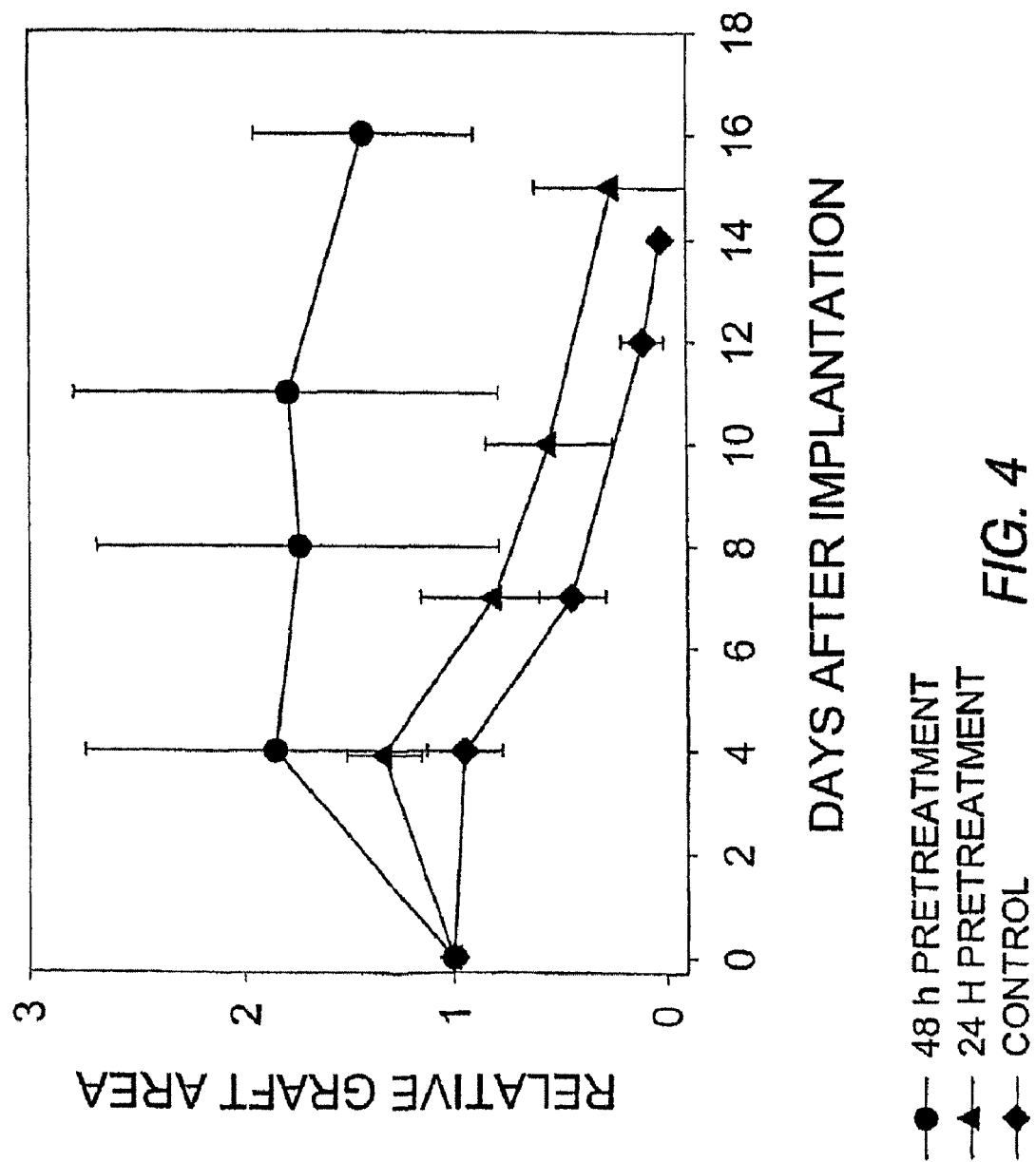
FIG. 4 is a graph which illustrates the effect of the time of administration of dextran on the survival of human HT1080 cell xenografts that are grown inside titanium chambers which have been implanted in C57BI/6 mice.

FIG. 4 shows the effect of the length of dextran pretreatment on the survival of xenografts. Twenty four hour pretreatment with dextran only slightly increases the survival of the xenograft relative to the control By contrast, when treatment is started 48 hours prior to spheroid implantation, the xenograft survival is greatly enhanced. The results presented in FIG. 4 together with those in Example 3 show that complete saturation of the APCs is required for effective inhibition of graft rejection.

Example 5

Inhibition of Allograft Stem Cell Rejection by Dextran Pretreatment

Allograft stem cells transplants were tested to examine if such cells would benefit from systemically administered poorly catabolized polymers. The methodology of Example 1 was used with the following modification. Beta stem cells from the pancreas derived from NOD mice stably transfected with green fluorescent protein, prepared as previously described (Ramiya et al, *Nature Medicine* 6:278-282 (2000)), were implanted into the chambers of C57BL/6 mice or Balb/c mice.

Figure 5:
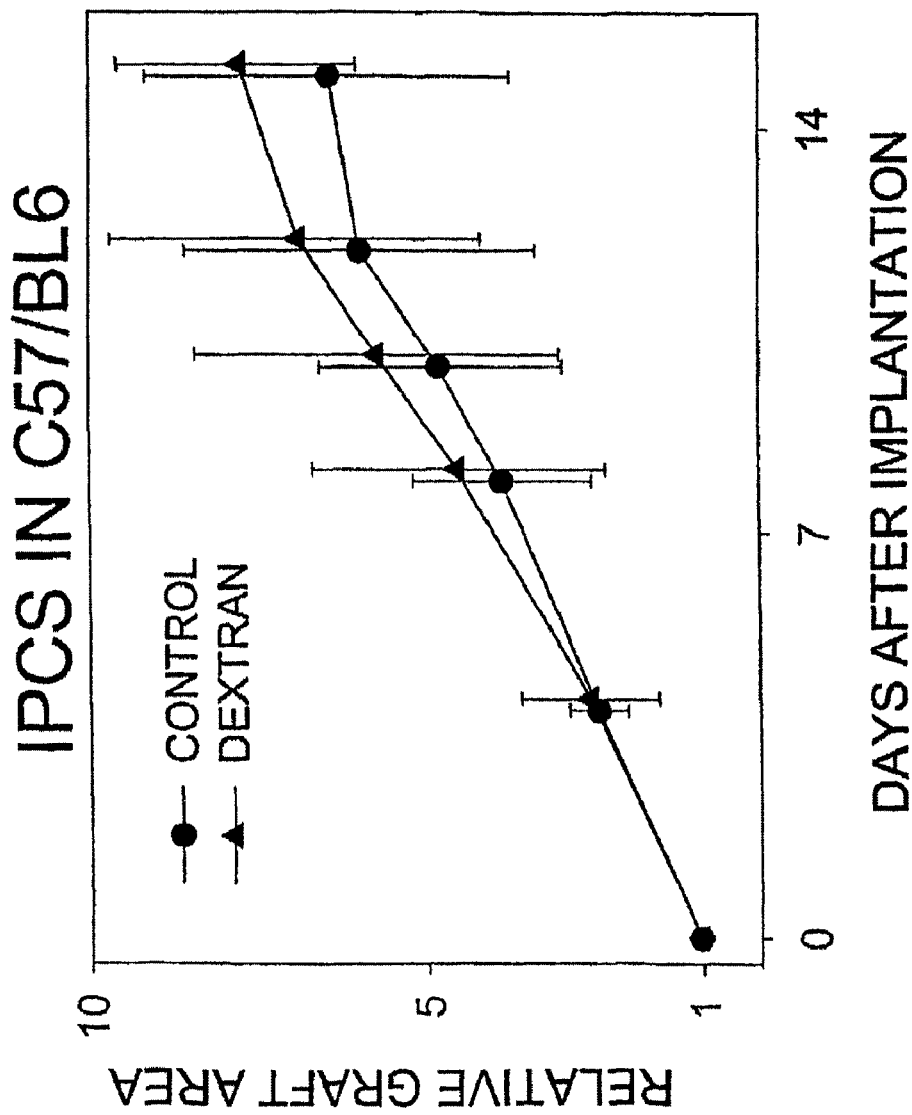
FIG. 5 is a graph which plots the survival of Murine NOD-derived beta stem cell isografts in immunocompatible C57BI/6 mice.

FIG. 5 plots the survival of beta stem cell grafts in C57BL/6 mice for both the control and treatment groups. A similar increase in graft size for both the control and dextran-treated mice is shown throughout the course of the experiment. These results indicate that systemic pretreatment with dextran had no significant effect on the growth of the beta stem cells spheroids that were grown as isografts in the chamber of C57BL/6 mice.

Figure 6:
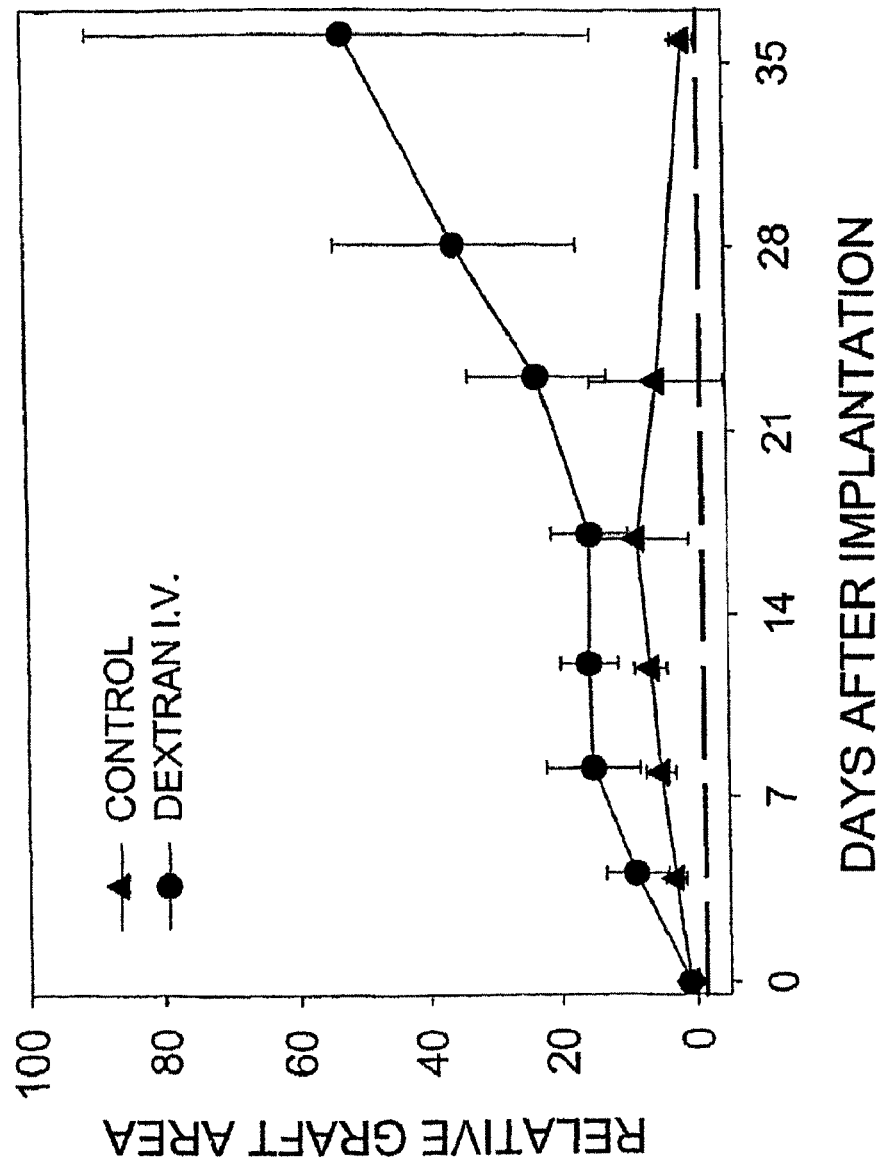
FIG. 6 is a graph which plots the survival of a Murine NOD-derived beta stem cell allograft in Balb/c mice.

By contrast, a significant difference in graft survival between the control and treatment groups for Balb/c mice can be observed. FIG. 6 shows that beta stem cell allografts fail to survive in untreated control mice by the end of the 35 day experiment. The beta stem cell allografts of the dextran-treated mice, however, show significant increase in size over the course of the experiment with a greater than 40-fold increase on day 35. These results and those from the previous examples demonstrate that both allografts and xenografts are protected by pre-administration with poorly catabolized polymers.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit and scope of that which is described and claimed.

What is claimed is:

1. A method of inhibiting rejection by the immune system of an antigenic material introduced into an animal comprising administering to the animal a composition comprising dextran having an average molecular weight of 500,000 daltons in advance of exposure to the antigenic material, thereby inhibiting rejection by the immune system of an antigenic material.

2. The method of claim 1, wherein the antigenic material is a cell.

3. The method of claim 1, wherein the antigenic material is from a gene therapy formulation.

4. The method of claim 2, wherein the cell expresses at least one antigen.

5. The method of claim 2, wherein the cell is an allografted cell.

6. The method of claim 2, wherein the cell is a xenografted cell.

7. The method of claim 2, wherein the cell is an isolated stem cell.

8. The method of claim 1, wherein the antigenic material is a formulation free of nucleic acids.

9. The method of claim 1, wherein the dextran is administered to the animal in the presence of other immunosuppressive agents.

10. The method of claim 1, wherein the dextran is non-immunogenic.

11. The method of claim 1, wherein the dextran is administered to the animal more than 24 hours prior to exposing the animal to the antigenic material.

12. The method of claim 1, wherein the dextran is administered to the animal at least 48 hours prior to exposing the animal to the antigenic material.

* * * * *